United States Patent
Ferguson

(10) Patent No.: US 7,284,859 B2
(45) Date of Patent: *Oct. 23, 2007

(54) LINE-SCAN LASER OPHTHALMOSCOPE

(75) Inventor: R. Daniel Ferguson, Melrose, MA (US)

(73) Assignee: Physical Sciences, Inc., Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/864,081

(22) Filed: Jun. 9, 2004

(65) Prior Publication Data

US 2005/0012899 A1    Jan. 20, 2005

Related U.S. Application Data

(63) Continuation of application No. 10/171,883, filed on Jun. 14, 2002, now Pat. No. 6,758,564.

(51) Int. Cl.
*A61B 3/10* (2006.01)

(52) U.S. Cl. .................................................. 351/205

(58) Field of Classification Search ............... 351/205, 351/206, 221; 606/4, 5; 600/473; 607/88, 607/89; 356/601, 606, 607, 608; 250/559.03, 250/559.22

See application file for complete search history.

(56) References Cited

U.S. PATENT DOCUMENTS 5,784,148 A * 7/1998 Heacock .................... 351/221
6,471,691 B1* 10/2002 Kobayashi et al. ............ 606/4

OTHER PUBLICATIONS

Kobayashi et al., "Confocal scanning laser ophthalmoscope with a slit aperature," J. Phys. Sci. Technol. 2, 287-292 (1991).
Heacock et al., "Imaging of the choroids with the scanning slit laser ophthalmoscope (SSLO)," SPIE vol. 3591, 456-464 (1999).

* cited by examiner

*Primary Examiner*—George Manuel
(74) *Attorney, Agent, or Firm*—Proskauer Rose LLP

(57) ABSTRACT

Systems and methods for providing a line-scanning laser ophthalmoscope (LSLO) are disclosed. The LSLO uses a substantially point source of light, such as an infrared laser or a super-luminescent diode. The point source is expanded to a line. The LSLO scans the line of light in a direction perpendicular to the line across a region of an eye having an undilated pupil The reflected light is received confocally, using monostatic beam geometry. A beam separator, such as a turning prism or mirror, diverts one of the incoming light and the reflected light to separate the light. An optical stop prevents non-confocally received light from reaching a one-dimensional detector, such as a linear CCD array. An electrical signal responsive to the output light at each of a plurality of locations along the line of output light is processed to provide images of the scanned portion of the eye.

27 Claims, 10 Drawing Sheets

Imaging System

Point Imaging / scanning

USAF Target

USAF Target

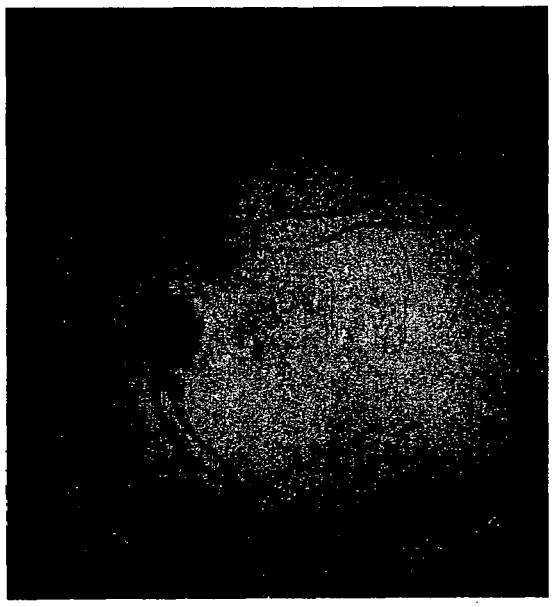 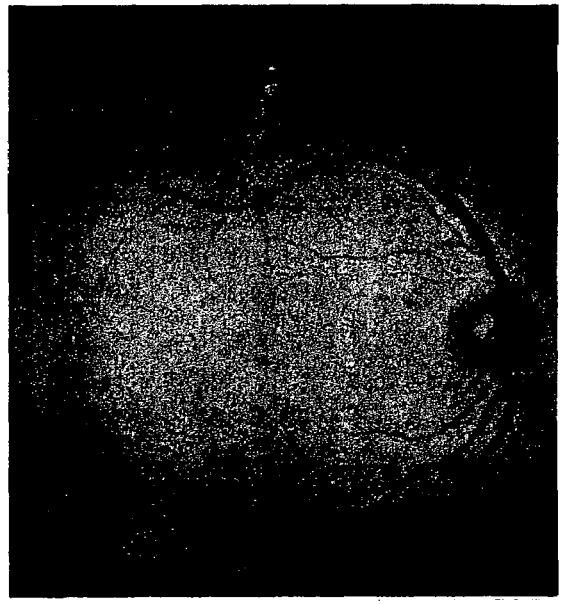
FIG. 7A  FIG. 7B
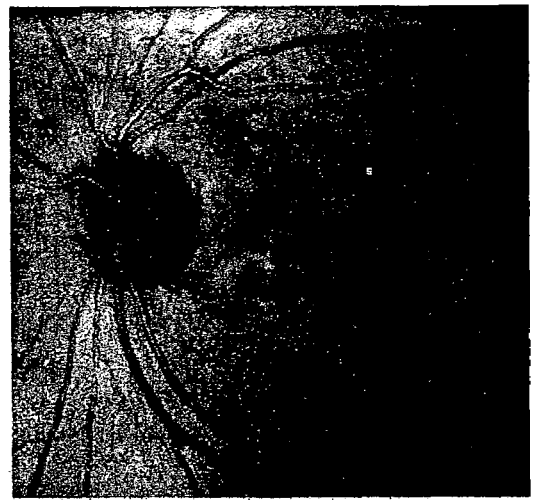
FIG. 8
PRIOR ART

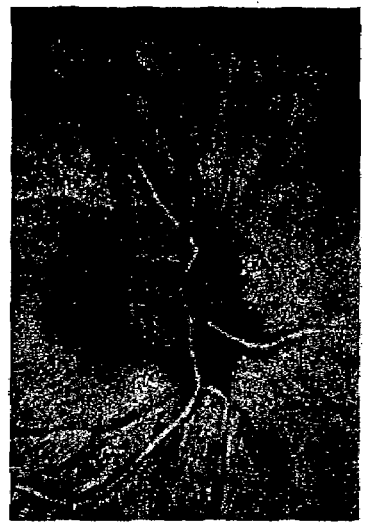 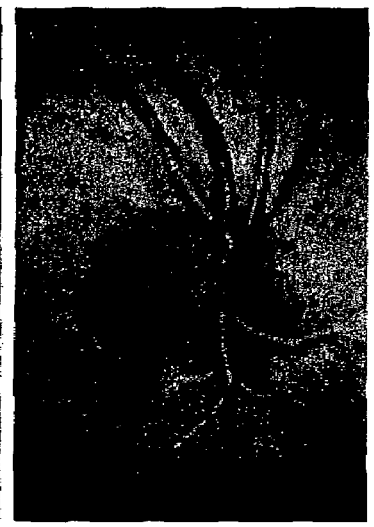
FIG. 10A  FIG. 10B
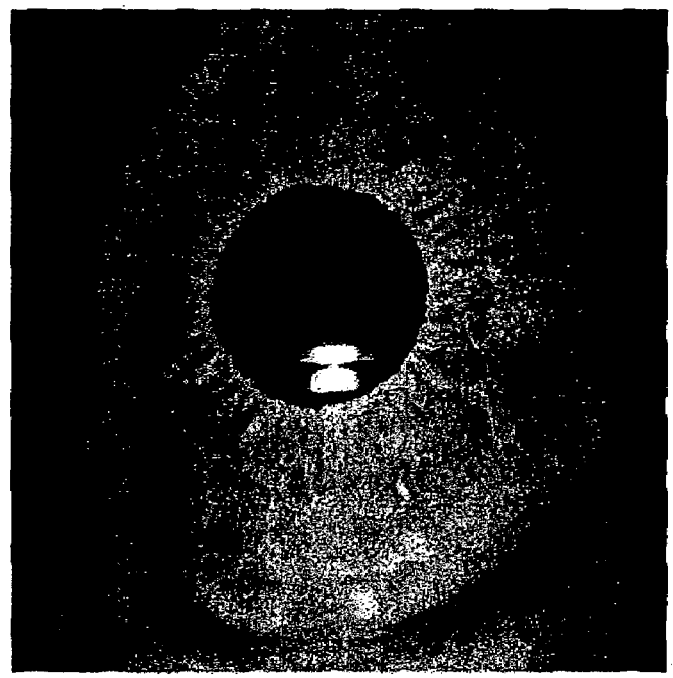
FIG. 11

LINE-SCAN LASER OPHTHALMOSCOPE

CROSS-REFERENCE TO RELATED APPLICATION

This application is a continuation of U.S. patent application Ser. No. 10/171,883 filed on Jun. 14, 2002, now U.S. Pat. No. 6,758,564 which is owned by the assignee of the instant application and the entire disclosure of which is herein incorporation by reference in its entirety.

GOVERNMENT RIGHTS

This invention was made with government support under Contract No. 1 R43 EY 11819-01A1 awarded by the National Institutes of Health/National Eye Institute. The government may have certain rights in the invention.

FIELD OF THE INVENTION

This invention relates generally to systems and methods for examining eyes. More particularly, the invention relates to systems and methods that employ scanned lines of light for examining eyes.

BACKGROUND OF THE INVENTION

Fundus imaging is the essential diagnostic procedure in ophthalmology. Instruments of the prior art that are useful for examining the fundus of the eye include direct and indirect ophthalmoscopes, the slit-lamp biomicroscope and the fundus camera. Complementary tools have been developed that broaden diagnostic and therapeutic possibilities, such as the Scanning Laser Ophthalmoscope (SLO). The SLO is a superior tool for rapidly and continuously acquiring high-contrast images of the ocular fundus and its structures, including the distribution of choroidal blood, melanin, and retinal pigments. Because it accommodates a variety of visible and NIR wavelengths, the SLO is especially useful for the study and early diagnosis of diseases such as age-related macular degeneration (AMD) and diabetic retinopathy. These are the leading causes of blindness in the elderly. The SLO is a powerful diagnostic tool for characterizing retinal pathologies, as well as for angiography, tomography, perimetry, and general psychophysics. Confocal SLO imaging is very effective in patients suffering from mild cataract, or from pathologies causing clouding of the vitreous. Another device for examining the fundus of the eye is the instrument described in U.S. Pat. No. 6,267,477, issued on Jul. 31, 2001 to Karpol et al. The Karpol instrument is described as operating on the principle of slit lamp bimicroscopy performed on an eye having a dilated pupil. The Karpol instrument uses a defined angle between a beam going to the retina and a beam returning from the retina, and there is a distance at the area of the pupil between the incident beam and the measured scattered beams. The Karpol instrument uses a two dimensional CCD camera as one of three cameras used to record images.

However, although they have become valuable diagnostic tools in the research community, scanning laser devices have not yet emerged into widespread clinical usage, due in part to their size, cost, and complexity. As a result, they are usually found only at specialized facilities, are used almost exclusively by ophthalmologists, and are often unavailable when needed. In particular, elderly and emergency patients are often unwilling or unable to travel to a specialized clinic for testing. But even the ubiquity of slit-lamps, fundus cameras and indirect ophthalmoscopes does not necessarily allow their use in many circumstances in which they may be indicated, such as emergency care. These devices may not be immediately accessible, and in many circumstances, the primary care physician may not choose to use instruments like Binocular Indirect Ophthalmoscopes (BIO's) which are more difficult to master, and may be unpleasant for the patient. The fallback device is the direct ophthalmoscope. The availability of hand-held and tele-ophthalmoscopic fundus imaging systems of the standard types are increasing, but their cost remains high, and they continue to have the limitations discussed. A portable, convenient, and less expensive system that provides high quality images of the fundus has been lacking.

SUMMARY OF THE INVENTION

The line-scanning laser ophthalmoscope (LSLO) of the invention has a significant confocal advantage in image clarity and contrast, and depth of penetration at the ocular fundus compared with conventional digital fundus photography. The LSLO has features not currently available in commercial SLOs, and is less expensive. The hand-held digital LSLO has proven that high quality, non-mydriatic (e.g., undilated pupil), line-confocal retinal images and stereo pairs can be obtained with a simple, compact design with fewer moving parts and components than current SLO systems. In one embodiment, the system and method involves a monostatic beam geometry, e.g., the light incoming to the thing to be observed, and the light collected in reflection from the thing, pass through the same location in space between the thing and the optical component nearest the thing. As a result of the monostatic beam geometry, the instrument can be operated with a small, undilated pupil. The instrument remains operative even if the pupil is dilated, however.

There are many benefits that accrue if the pupil of an eye is not required to be dilated for the systems and methods of the invention to function correctly. Dilation is generally performed by applying chemicals topically and waiting for the dilation to occur. The waiting period can be some minutes, typically twenty minutes. Absence of a dilation requirement means that an instrument embodying principles of the invention can be used immediately, rather than only after a delay necessitated by the dilation of the pupil. This allows use in settings such as emergency or field use, where other instruments become useful only after the dilation of the pupil is complete. Dilation of the pupil causes the patient to have reduced visual acuity for periods of up to hours, until the effect of the dilation chemicals wears off. Dilation of the pupil can require a patient to use protective eyewear or to avoid light of ordinary intensity. Dilation of the pupil can cause a patient discomfort. The use of an instrument embodying principles of the invention can eliminate all of the above negative features of dilation of the pupil.

The inventive technology provides an affordable clinical instrument that gives the clinician the power and resolution of the SLO, with some operational features of the most familiar ophthalmic diagnostic instruments, in an untethered package that is comparable in size and weight to commercial hand-held digital video cameras.

The LSLO can provide stereo fundus images. A binocular LSLO, with low-cost wearable display technology and more deeply penetrating near-infrared (NIR) light, can provide real time 3-D morphometric information that is usually the domain of slit-lamp biomicroscopes, binocular indirect ophthalmoscopes (BIOs), and stereo fundus photography at shorter wavelengths. NIR operation increases patient comfort and reduces the risk of phototoxicity during extended exams or procedures. By incorporating additional laser wavelengths as additional channels for particular wavelength combinations, color information can be captured and fused with NIR images. The digital LSLO allows the operator to switch views between live-motion and captured still images with the touch of a button. Synchronous modulation of laser illumination with line-by-line image acquisition and variable scans allows stereo images, dual-color images, or fluorescence images to be multiplexed and recorded. The LSLO can be quickly reconfigured for anterior segment imaging, pupil size and light response. The compact and lightweight LSLO offers the potential for use as a hand-held emergency care aid, particularly with blood in the vitreous from eye or head trauma. A portable digital LSLO which performs some of these functions at a cost approaching indirect ophthalmoscopes, while retaining much of the confocal and NIR advantages of the SLO, becomes more clinically versatile and commercially attractive.

In one aspect, the invention relates to a line-scanning laser ophthalmoscope (LSLO). The LSLO comprises a light source providing a substantially point source of light; an optical apparatus and a one-dimensional detector. The optical apparatus comprises an optical component that accepts the light from the laser and provides a line of incoming light, at least one optical component that (i) scans a portion of an eye with the incoming line of light in a direction perpendicular to the line, (ii) confocally receives reflected light from the illuminated portion of the eye, and (iii) provides output light in a line focus configuration; and a turning mirror that redirects a selected one of the incoming light and the reflected light. The one-dimensional detector detects the output light and provides an electrical signal responsive to the output light at each of a plurality of locations along the line of output light.

The light source providing a substantially point source of light comprises a laser. Alternatively, the light source providing a substantially point source of light comprises a super-luminescent diode. The optical component that accepts the light from the light source and provides a line of light comprises one or more lenses. Alternatively, the optical component that accepts the light from the light source and provides a line of light comprises a holographic optical element.

In one embodiment, the LSLO further comprises a signal analysis module that decodes electrical signals from the one-dimensional detector and that generates an array of data representative of reflected light from the illuminated portion of the eye.

In one embodiment, the LSLO further comprises a display module that displays information representative of the array of data generated by the signal analysis module. The one-dimensional detector is a linear CCD array or a linear CMOS array in some embodiments. In a preferred embodiment, the laser is an infrared laser. In a more preferred embodiment, the infrared laser operates at a wavelength in the range of 700 nm to 950 nm. In a still more preferred embodiment, the infrared laser operates at a wavelength of substantially 830 nm.

In some embodiments, the optical apparatus of he LSLO further comprises a scanning mirror that provides a scanned line of light having a scan direction perpendicular to the line of light, one or more lenses that focus the scanned line of light on a portion of an eye, one or more lenses that confocally receive reflected light from the illuminated portion of the eye and provide a line of reflected light, a scanning mirror that redirects the line of reflected light, a pupil stop that prevents unwanted light from proceeding through the optical apparatus, and an objective lens that focuses the redirected line of reflected light onto the one-dimensional detector.

In a preferred embodiment, the scanning mirror that intercepts the redirected line of light and provides a scanned line of light and the scanning mirror that redirects the line of reflected light are the same scanning mirror. In a preferred embodiment, the one or more lenses that focus the scanned line of light on a portion of an eye and the one or more lenses that confocally receive reflected light from the illuminated portion of the eye are the same one or more lenses. In some embodiments, the pupil stop prevents non-confocally received light from proceeding through the optical apparatus.

In still another aspect the invention features a line-scanning ophthalmoscope. The line-scanning ophthalmoscope comprises a light source providing a substantially point source of light, an optical apparatus and a one-dimensional detector. The optical apparatus (i) receives light from the light source, (ii) scans a portion of an eye with the line of light in a direction perpendicular to the line, (iii) confocally receives reflected light from the illuminated portion of the eye, and (iv) provides output light in a line focus configuration. The one-dimensional detector detects the output light and provides an electrical signal responsive to the output light at each of a plurality of locations along the line of output light.

In yet a further aspect, the invention relates to a line-scanning laser ophthalmoscope (LSLO). The LSLO comprises a light source providing a substantially point source of light; an optical apparatus and a one-dimensional detector. The optical apparatus comprises an optical component that accepts the light from the laser and provides a line of incoming light, at least one optical component that (i) scans a portion of an eye having an undilated pupil with the incoming line of light in a direction perpendicular to the line, (ii) confocally receives reflected light from the illuminated portion of the eye, and (iii) provides output light in a line focus configuration, and a turning mirror that redirects a selected one of the incoming light and the reflected light. The one-dimensional detector detects the output light and provides an electrical signal responsive to the output light at each of a plurality of locations along the line of output light.

In a further aspect, the invention relates to a line-scanning laser ophthalmoscope (LSLO). The LSLO comprises a light source providing a substantially point source of light; an optical apparatus and a one-dimensional detector. The optical apparatus comprises an optical component that accepts the light from the laser and provides a line of incoming light, at least one optical component that (i) scans a portion of an eye with the incoming line of light in a direction perpendicular to the line, (ii) confocally receives reflected light from the illuminated portion of the eye, the incoming line of light and the reflected light having monostatic beam geometry, and (iii) provides output light in a line focus configuration, and a turning mirror that redirects a selected one of the incoming light and the reflected light. The one-dimensional detector detects the output light and provides an electrical signal responsive to the output light at each of a plurality of locations along the line of output light.

In a further aspect the invention relates to a method of making a optical measurement of an object. The method includes the steps of providing an incoming line of light, scanning a portion of an object with the incoming line of light in a direction perpendicular to the line, confocally receiving reflected light from the illuminated portion of the object, providing output light in a line focus configuration from the received reflected light, separating the incoming light and the output light, detecting the output light, and providing an electrical signal responsive to the output light at each of a plurality of locations along the line of output light. In one embodiment, the object is an eye. In one embodiment, the method further comprises the steps of decoding the electrical signal, and generating an array of data representative of reflected light from the illuminated portion of the object.

In still a further aspect, the invention includes a method of making an ophthalmoscopic measurement. The method includes the steps of providing an incoming line of light, scanning a portion of an eye having an undilated pupil with the incoming line of light in a direction perpendicular to the line, confocally receiving reflected light from the illuminated portion of the eye, providing output light in a line focus configuration from the received reflected light, separating the incoming light and the output light, detecting the output light, and providing an electrical signal responsive to the output light at each of a plurality of locations along the line of output light.

In yet an additional aspect, the invention relates to a method of making an ophthalmoscopic measurement. The method includes the steps of providing an incoming line of light, scanning a portion of an eye with the incoming line of light in a direction perpendicular to the line, and confocally receiving reflected light from the illuminated portion of the eye, using a monostatic beam geometry for the incoming line of light and the reflected light. The method also includes the steps of providing output light in a line focus configuration from the received reflected light, separating the incoming light and the output light, detecting the output light, and providing an electrical signal responsive to the output light at each of a plurality of locations along the line of output light.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 7 shows forty degree field LSLO images in the left and right eyes of a human subject, according to principles of the invention;

FIG. 8 shows a standard SLO image of the prior art;

FIG. 10 shows illustrative disc image pairs captured in succession with the LSLO, according to principles of the invention; and FIG. 11 is an image that illustrates confocal and anterior segment imaging, according to principles of the invention.

DETAILED DESCRIPTION

The digital LSLO instrument can be used as a relatively inexpensive multi-mode screening tool to facilitate rapid, non-mydriatic exams for large numbers of patients. In some embodiments of the invention, rapid is to be understood as connoting real time operation. As a portable device, the instrument aids in the early detection of AMD, and other diseases of the elderly, where no economical early warning methods currently exist. The digital LSLO complements existing diagnostics and tele-medicine screening tools for detecting onset of diabetic retinopathy. Many elderly patients may have difficulty in adapting their posture to the demands of any of the standard instruments. Pediatric examination has similar constraints. Instead, instruments should adapt to the needs of the patient. The compact and lightweight LSLO may be used as a hand-held primary care and emergency care aid. The LSLO according to principles of the invention is advantageously used without the necessity to dilate a pupil of an eye, and employs a monostatic beam geometry. At sufficiently low cost, simplified versions of the LSLO may be used by EMTs for head trauma where anomalous bulging of the optic disk is indicative of elevated intracranial pressure, or with blood in the vitreous, as well as for stereo examination of the anterior segment and recording of pupil size and response. High-quality images of injured ocular structures can be captured in a fraction of a second, and transmitted to a treatment center for diagnosis and advice. Veterinary applications include animal certification and identification.

Figure 1:
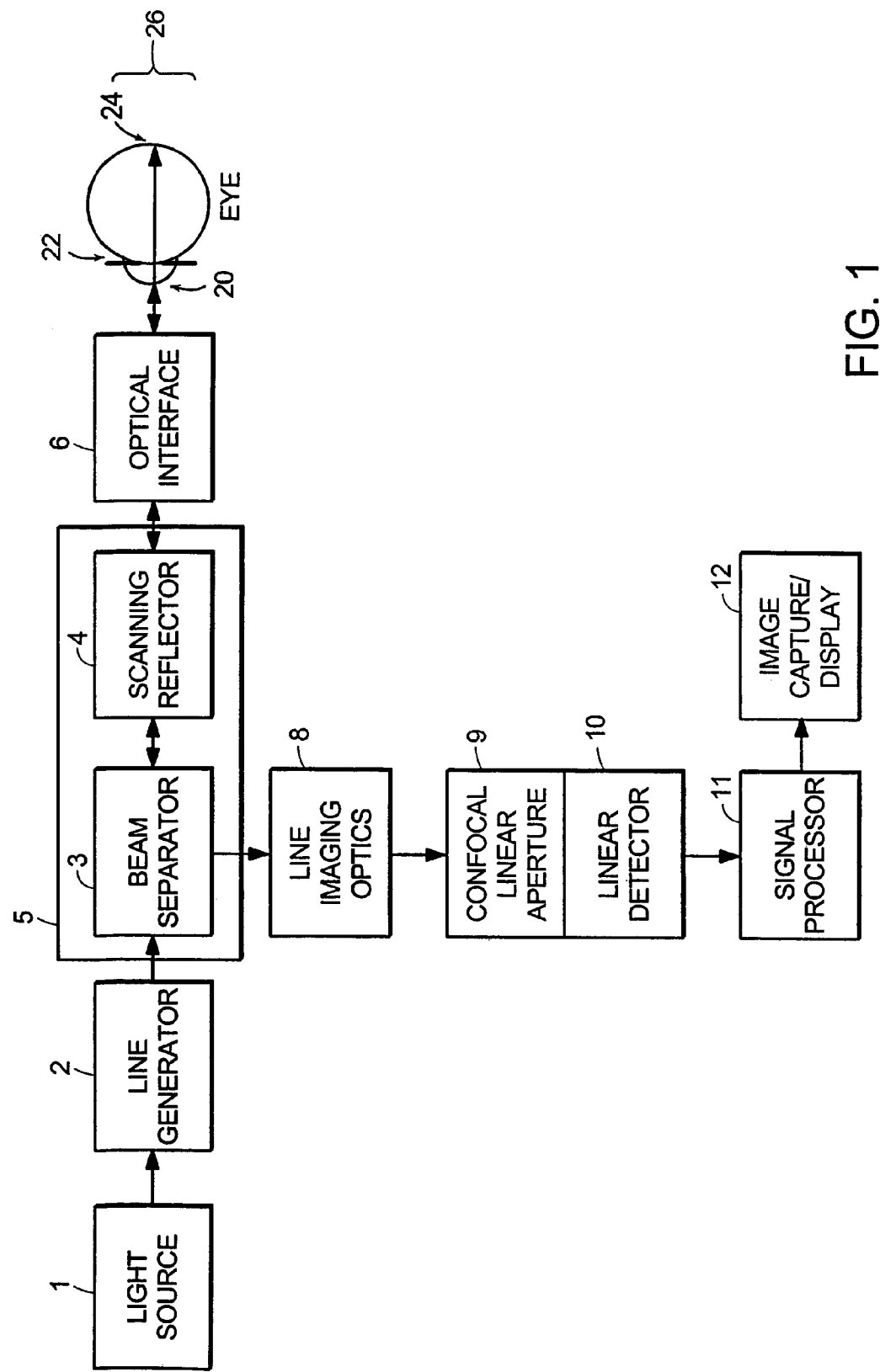
FIG. 1 is a schematic diagram showing an embodiment of a line scanning imaging system, according to principles of the invention.

Referring to FIG. 1, an embodiment of a line scanning imaging system is shown in schematic form. FIG. 1 can also be viewed as a schematic diagram showing the steps of a process, such as a method of use of the imaging system, in which each step is represented by a box in the diagram. A light source 1, which in some embodiments is a laser or a super-luminescent diode, provides a substantially point source of light. In some embodiments, the light is infrared light. In other embodiments, light within the spectral range from the ultraviolet through the infrared may be provided. The light is received in a line generator 2 and is converted to a line of light. In some embodiments, the line generator 2 is one or more lenses, or a holographic optical element. The line of light from the line generator 2 impinges on a beam conditioner 5 that includes a beam separator 3 and a scanning reflector 4. The line of light interacts with the beam separator 3 and the scanning reflector 4 in either of two sequences. In some embodiments, the line of light interacts with the beam separator 3 before reaching the scanning reflector 4, for example in an embodiment in which the beam separator is a turning mirror or turning prism that intercepts the line of light as it travels in what will be referred to as the incoming direction, e.g., the direction of travel toward the object to be examined or imaged. In other embodiments, the beam separator 3 is a turning mirror or turning prism that receives returning light that has been reflected from the object to be examined or imaged. In either circumstance, the beam separator 3 and the scanning reflector 4 are configured to oblige the incoming light and the returning light to follow separate paths, respectively, between the light source and the beam conditioner 5, and between the beam conditioner 5 and the linear detector 10 (which will be further described below). An optical interface 6 such as one or more lenses receives a line of light that scans in a direction perpendicular to the line, and focuses the light on an adjacent object 7 to be examined.

In the embodiment depicted in FIG. 1, the object 7 is a human eye. The eye 7 includes a cornea 20, a pupil 22 and a retina 24. The eye 7 includes a region referred to generally as a fundus 26, which is the interior rear wall of the eye 7. In other embodiments, the object 7 to be examined or imaged is a mammalian eye, or the object 7 is an object of interest that has optical attributes that are subject to examination by a scanned line of light. The incoming line of light is scanned across a portion of the object 7 such as the fundus 26 of the eye. As is well understood, light that impinges an object can be affected in three ways. The light can pass through the object in transmission, the light can be absorbed by the object and may also be re-emitted, and the light can be reflected by the object. For an object of interest such as the eye 7, there will be reflections from some regions of the eye 7, including the front surface of the cornea 20, and the front surface of the fundus 26. Some structures in the eye 7 will absorb and re-emit some of the light, such as layers from the front of the fundus 26 and below the fundus 26. The transmission, absorption/re-emission, and reflection properties of different portions of the object 7 will in general be a function of the wavelength of the incoming light, and will also depend on the structure and composition of the regions of the object 7.

The light that returns to the line-scanning imaging apparatus from the object 7 is a light in the form of a line, which is the reflection and or the absorption and re-emission of the incoming line of light. It is also possible that extraneous light may enter the apparatus, for example as a consequence of operating the apparatus in an environment where ambient light is present. The returning light, which for simplicity will be described as reflected light, is received confocally by the optical interface 6. Depending on the configuration of the beam separator 3 and the scanning reflector 4 in the beam conditioner 5, the returning light is reflected by the scanning reflector 4 in a synchronous manner with the scanning of the incoming line of light, so that the reflected light passes to the line imaging optics 8. The line imaging optics 8 reconfigures the reflected light into a line. The line of reflected light passes a confocal linear aperture 9 and impinges on a linear detector 10. In one embodiment, the beam conditioner 5 is configured to position the beam separator 3 at the conjugate to the cornea 20, and to position the scanning reflector 4 at the conjugate to the pupil 22. In one embodiment, the confocal linear aperture 9 is positioned to be conjugate to the line illumination on the retina 24. The confocal linear aperture 9 can be designed to prevent light that is not confocally received by the apparatus from passing through to the linear detector 10. In one embodiment, the linear detector 10 is a linear CCD array detector, such as a 1×512 pixel linear array. In another embodiment, the linear detector 10 is a 1×N linear CMOS array, where N is an integer greater than 1 representing the number of pixels in the array.

The electrical signals generated within the linear detector 10 pass to an electrical signal processor 11, such as an analog-to-digital (A-to-D) converter that converts analog light levels to digital signals. The signal processor 11 is connected to a processing apparatus such as a commercially available personal computer that can receive, store, and analyze the electrical signals in digital form, for example by use of a frame grabber. The A-to-D and the computer are optionally connected to an image/capture/display module 12, which can include any of a computer monitor or video display, a printer, a plotter, a machine-readable storage medium such as one or more of electronic, magnetic and optical storage media (e.g., memory chips, magnetic disks, CD-ROM, DVD), and an enunciator such as a speaker. In one embodiment, the apparatus is portable, and the linear detector 10 and signal processor 11 apparatus are miniaturized and are provided on one or more semiconductor chips. As is well known in the art, power supplies and motors (which are not shown in FIG. 1) are provided to operate the scanning reflector 4, the light source 1, the linear detector 10, and the signal processor 11. The image capture/display 12 can in some embodiments be a small viewable electronic display, such as is found in a portable television, a cellular telephone, or a personal digital assistant. In some embodiments, the image capture/display 12 is a remote display, for example a display situated in the office of a consulting specialist, who receives the image via a connection such as telephone, television, internet, 25 satellite transmission, or optical fiber interconnection, and who examines the image and provides an opinion thereon.

Different embodiments of apparatus employing principles of the invention include a compact, portable, affordable multi-function LSLO device for confocal visible and NIR imaging, including stereoscopic and dual wavelength operation, and digital image capture and transmission. Such a device is attractive in applications ranging from screening in the elderly to pediatric examination, and from field use or emergency care to veterinary medicine. For example, in field use, high-quality images of injured ocular structures can be captured in a fraction of a second, and transmitted to a treatment center for diagnosis and advice. Veterinary applications include animal certification and identification.

In one embodiment, the line of light is produced by a laser as the light source 1 operated with a fixed cylindrical optic as the line generator 2. The line of light is itself eye-safe for extended periods, even if the scanning reflector 4 should fail, because the laser light can never focus to a point in any failure mode. In other words, the apparatus is inherently safer than scanning spot systems. The apparatus presents minimal risk to human subjects without the need for extensive failsafe engineering.

Figure 2A:
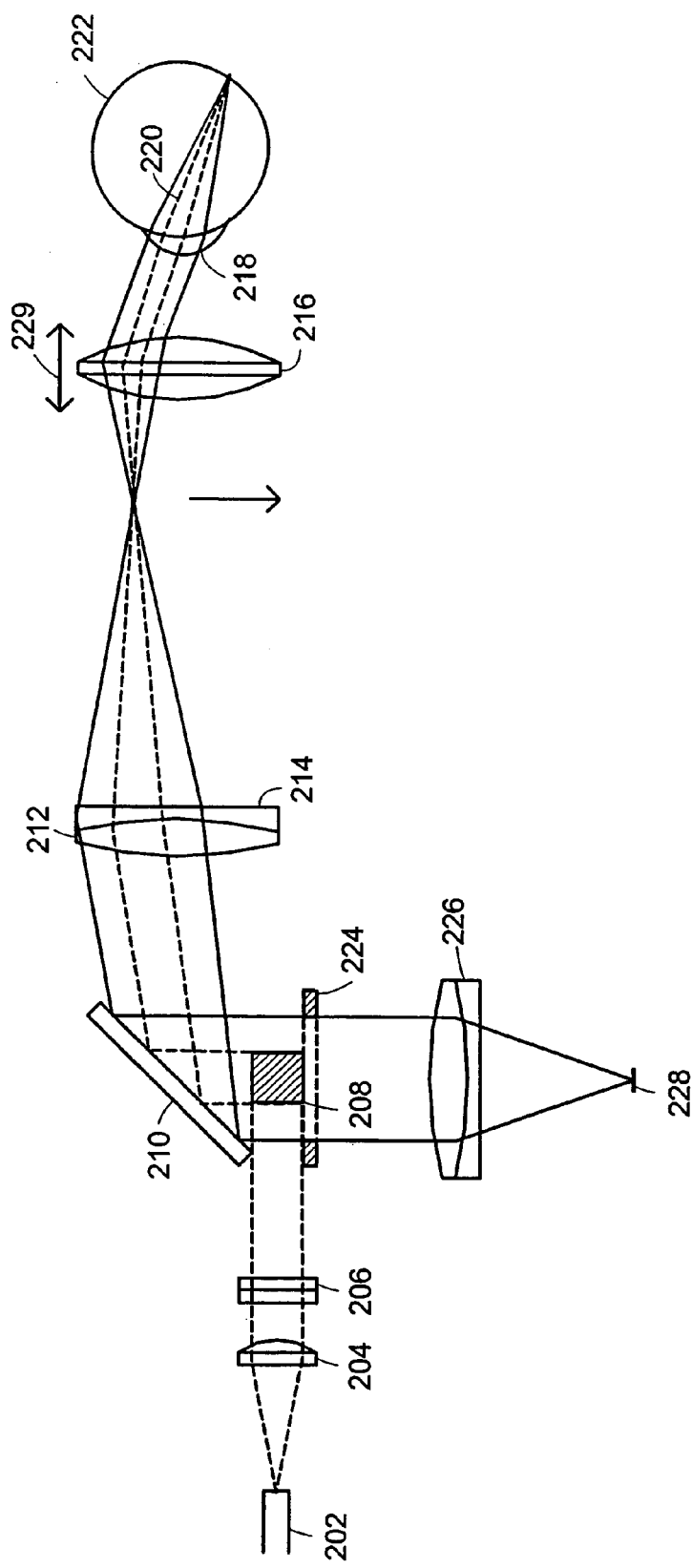
FIG. 2A is a side view of the optical layout of an illustrative line-scanning laser ophthalmoscope that embodies principles of the invention.

FIG. 2A is a side view of the optical layout of an illustrative line-scanning laser ophthalmoscope ("LSLO") that embodies principles of the invention. The LSLO is a simple, compact device which scans a focused laser line on the fundus. A laser 202 provides a substantially point source of light. In the embodiment of FIG. 2A, the light is expanded to a line of light by lenses 204, 206 which are cylindrical lenses. Other optical components can be substituted for the cylindrical lenses 204, 206 to transform he substantially point source of light into a line of light. The line of light impinges on the turning prism or mirror 208, and is redirected to the scanning mirror 210. The scanning mirror 210 is caused to move by a drive, such as a galvanometer motor drive known in the art for driving mirrors. The line of light is scanned by the scanning mirror 210 and passes through one or more lenses 212, 214, 216 which are positioned and/or adjusted to pass the line of light through a cornea 218 of an eye and through an undilated pupil 220 of the eye so as to impinge as a line focused on a fundus 222 of the eye, which includes the retina of the eye.

The reflected light exits the eye through the pupil 220 and the cornea 218, passes through the one or more lenses 216, 214, 212, is redirected by the scanning mirror 210 such that reflected light passes around the turning mirror 208 and passes through the pupil stop 224, reaching and passing through one or more objective lenses 226. The laser line is imaged by the lenses 216, 214, 212, 226 confocally to a linear CCD array 228. In one embodiment, the linear CCD array 228 is a DALSA camera with 512 14 μm pixels. A single galvanometer-driven mirror 210 performs the scan transverse to the laser line. The linear CCD readout is synchronized with scan motion and acquired with a frame grabber. A rectangular image of the fundus is thus obtained.

In one embodiment, the 830 nm laser diode is connected to the optical assembly of the LSLO via an FC fiber cable. 830 nm is an advantageous wavelength to use, because the human eye is insensitive to that wavelength, while infrared detectors having reasonable sensitivity are available. Accordingly, there is little or no pupillary reflex to the light, and little discomfort for the subject of the examination. Other infrared wavelengths can also be used to advantage. By comparison, the human eye reacts strongly to visible light, with both contraction of the pupil and potentially, discomfort and a reaction involving motion of the eye. In the illustrative instrument, commercially available lenses are employed. The digital camera is a commercially available DALSA digital line-scan camera Model CB512, having a linear CCD array 228 (1×512) of 14 μm square silicon pixels. The gain in this model is not fully adjustable. Gain compensation is attained by operation at slower scan rates than would otherwise be possible. Different linear CCD arrays 228 with increased gain may be advantageously used.

The DALSA camera body houses a number of low-density circuit cards. The linear CCD array itself is quite compact. A focus adjustment for the laser, and line rotation and displacement adjustments to align the laser line with the linear CCD array are provided with standard Newport tip/tilt mounts, rotary mounts, and slidemounts. The line confocal system is quickly aligned and optimized over the length of the array. The ophthalmoscopic lens slide is used solely to correct for a very large range of ametropia.

In one embodiment, power and computer cables (not shown) attach to the bottom of the DALSA camera body. In a portable embodiment of the LSLO, the connections are eliminated and on-board batteries and an embedded computer are employed. In one embodiment, the device weighs about 3 pounds, and can be lifted and manipulated rather easily.

In one embodiment, the LSLO configuration uses a single-mode fiber coupled 3 mW 830 nm laser 202 with an approximately gaussian profile. The laser is collimated and passed through a fixed cylindrical optic 204, 206 having 25 mm focal length. The beam remains collimated on one transverse axis, but focuses near the pupil conjugate and then rapidly diverges on the other transverse axis. A 5 mm clear aperture prism mirror 208 turns the beam into the optical train, and also acts as a pupil stop 224 for pupil reflection and some scattered light, according to the Gull-strand principle. The galvanometer driven mirror 210 near this pupil conjugate vertically scans the beam. It has a 14 mm clear aperture. This pupil conjugate is imaged to the eye pupil with the scanning lens 212 (80 mm) and two ophthalmoscope lenses 214, 216, either the Volk Super 66 or the Volk 30D (66 or 30 diopters), all with NIR anti-reflection coatings. The 830 nm-optimized achromat scanning lens 212 was selected to produce a near diffraction-limited line at the retinal conjugates with good field flatness. These lenses are larger than necessary and are chosen merely for convenience, availability and cost.

The pupil magnification at the turning mirror 208 (a pupil conjugate) with the Volk 66 is 5×, and the beam size at the eye entrance pupil 220 is 1 mm (2.4× magnification and ~2 mm pupil for the Volk 30D). The measured power at the pupil 220 is less than 2 mW. The eye focuses the beam to near the diffraction limit in the vertical axis on the retina 222, but fans the beam rapidly on the other axis. This reduces the power density at the retina 222, relative to a diffraction-limited spot, by a factor of more than 500, e.g., the aspect ratio of the laser line. For reflected light, the same magnifications give the corresponding size of the scanning mirror aperture at the exit pupil: for the Volk 66, the exit pupil is 3 mm, and for the 30D, as much as 6 mm. In the latter case, the iris of the eye usually will be the limiting stop. As long as the pupil is large enough to collect light around the illumination pupil stop, the LSLO will function. The collected de-scanned light is imaged by the objective lens onto the linear CCD array. The lens selected is a 40 mm achromat, but is neither optimized at 830 nm, nor AR-coated. This lens is less critical but will affect in-line resolution to some extent. The use of custom lenses may allow optimization at a selected wavelength.

Figure 2B:
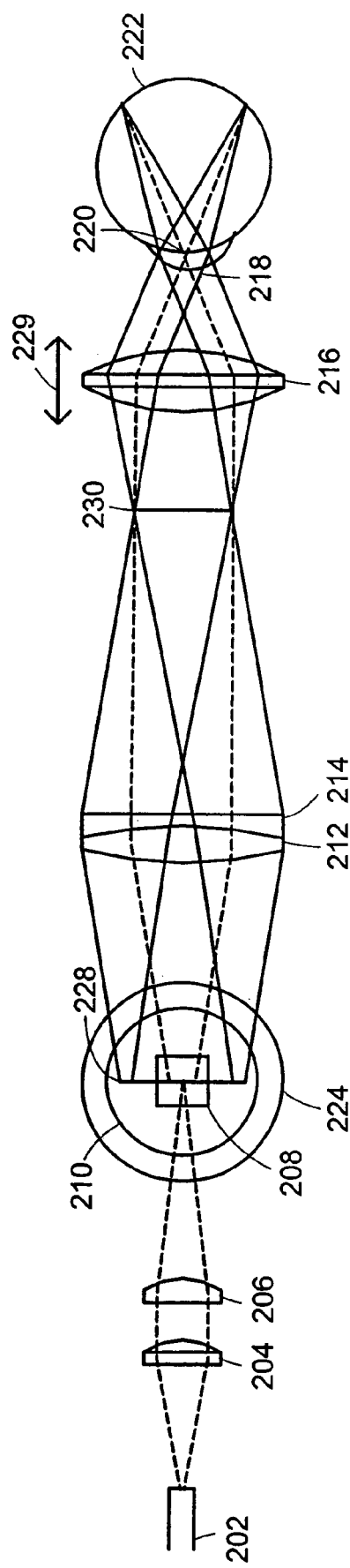
FIG. 2B is a top view of the optical layout of the illustrative line-scanning laser ophthalmoscope that is depicted in FIG. 2A.

FIG. 2B is a top view of the optical layout of the illustrative line-scanning laser ophthalmoscope that is depicted in FIG. 2A. Both the top and side view are shown because the cylindrical optic 204, 206 requires both tangential and sagittal views to visualize its operation. The side view shows the pupil separation at the small turning prism mirror 208 that allows the illuminating (incoming) beam to pass to the retina 222 while acting as a stop for corneal reflections. In this view, the LSLO is indistinguishable from its point-scanning cousin, the SLO. The top view shows the action of the cylindrical lens 204, 206 which focuses at the pupil conjugate and diverges to a tightly focused laser line 230 at the retina 222. The line 230 is scanned on the retina 222 by the scanning mirror 210 and the reflection is des-canned and imaged to the linear CCD array 228. The LSLO of the present invention preserves advantages such as rejection of interfering scattered light, and rejection of light scattered from defocused planes above and below the focal plane, even though an entire line is imaged at once.

Both transverse and longitudinal characteristics of the imaging systems of the invention should be considered in describing the theoretical performance limits of the systems. Diffraction at the focal plane, and scattered light reflected from other defocused planes are analyzed. The purely focal plane case, as with a planar target such as a resolution chart, is to be distinguished from volume targets such as biological tissues that reflect light from multiple planes. In the following, "focal plane" is understood to mean a conjugate to the image plane where the detector or confocal aperture lies.

Figure 3:
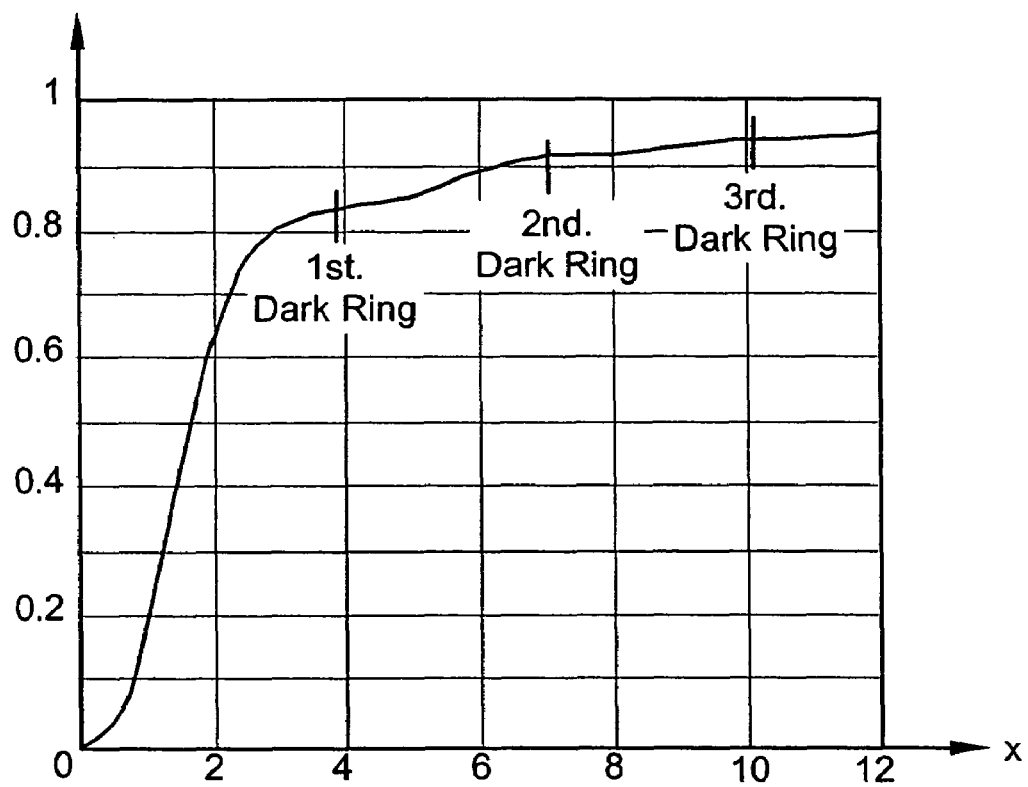
FIG. 3 is a diagram showing the integrated power falling within a circle of a given radius, according to the prior art.

One characteristic of an imaging system is its Modulation Transfer Function (MTF) or equivalently its Point Spread Function (PSF). These functions describe how the image of a point source is broadened in the image plane. In a diffraction limited system imaging diffuse reflections, the PSF is the familiar Airy pattern for reflected light emerging from the target and filling the collection aperture. The integrated power falling within a circle of a given radius is shown in FIG. 3, which is well known in the prior art. In the focal plane case, one can think of the interfering light as contributions from the wings of the total PSFs, including aberrations, of adjacent illuminated regions. The farther away these imaged points are from a particular confocal aperture (or pixel), the weaker their contribution to the background light. The total power at any given pixel is the sum of all such contributions over the entire illuminated area (ignoring scattering). When used to probe a cavity such as the eye, the SLO is ideal and nearly background-free because there are no other illuminated regions: the "flying spot" is the only light source. The total LSLO background pixel power is effectively a line integral along a strip through the center of the PSF since only a line of illumination is used. As a result of the linear scan, there are contributions from the left and right of each pixel, but the regions above and below the line are dark. Ordinary CCD imaging however, is a complete surface integral over the PSF, to the limits of the illuminated area. The limiting contrast is found from FIG. 3 by reading the percentage of total energy at the central pixel's edge, whatever its size may be. The focal image contrast is best for the SLO, and worst for standard fundus imaging. The LSLO lies somewhere in between. The sharper the PSF relative to the pixel size, the smaller the difference in focal plane performance of the LSLO relative to that of the SLO.

The contribution of out-of-focus regions above and below the plane of focus need to be considered for the case of a volume scattering medium. A significant performance enhancement can be realized with confocal imaging. Three imaging schemes are illustrated in FIGS. 4A-4C.

Figure 4A:
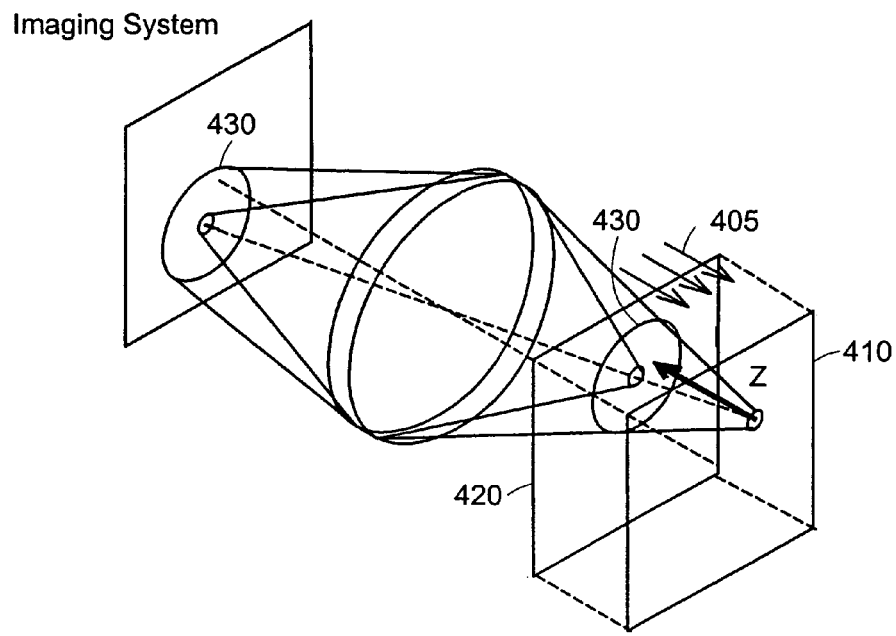
FIG. 4A illustrates the optical effect of defocusing in a prior art full field imaging method.
Figure 4B:
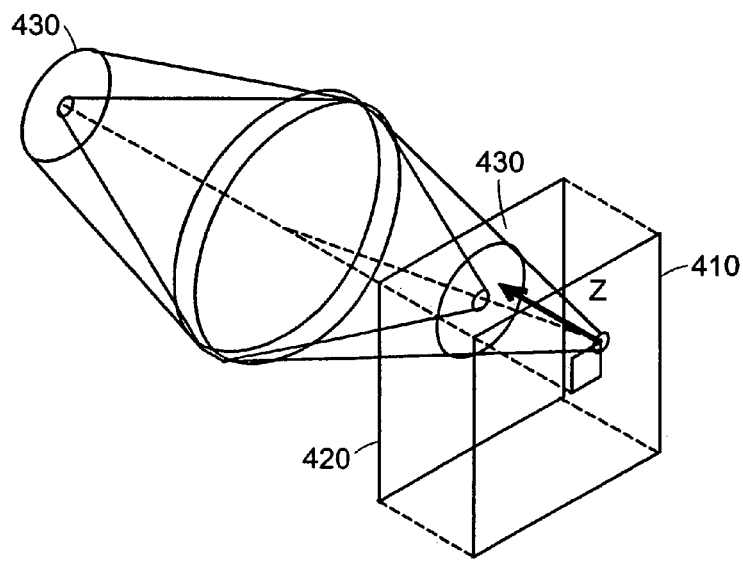
FIG. 4B shows the optical effect of defocusing in a confocal "flying spot" system of the prior art.
Figure 4C:
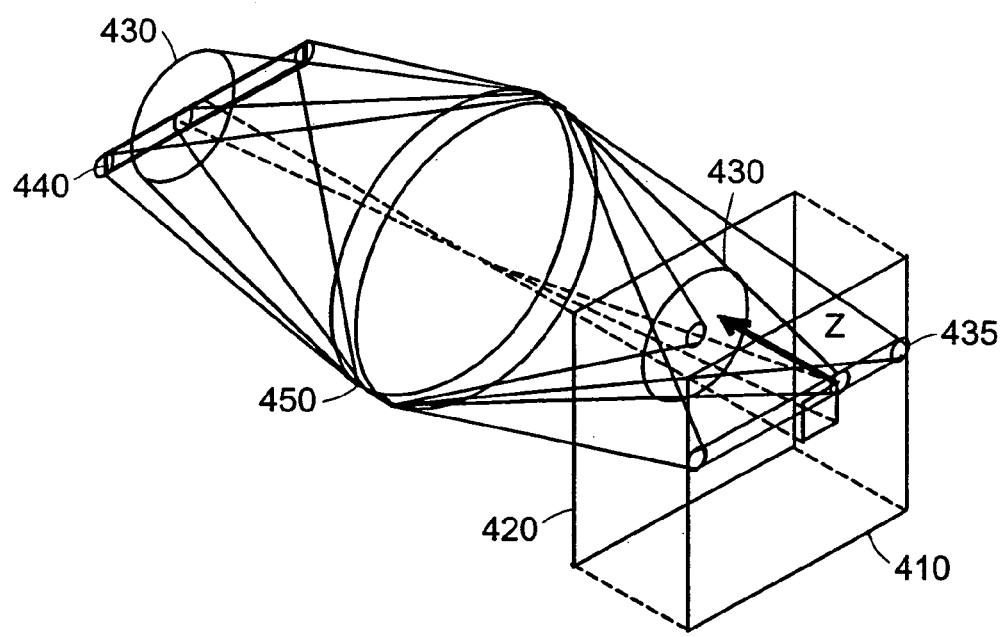
FIG. 4C illustrates the optical effect of defocusing in a line scanning imaging system such as the LSLO of the invention.

FIG. 4A illustrates the optical effect of defocusing in a prior art full field imaging method. When the media above or below the focal plane scatters light, the use of full field illumination results in a severe defect, as will be explained. In FIG. 4A, uniform light 405 impinges on a focal plane 410. A reflection at a defocused plane 420 at distance Z from the focal plane 410 will provide a defocused image 430 comprising a large blur circle at the detector plane. The behavior of the intensity with Z is analyzed for three cases, namely full field imaging, "flying spot" imaging, and line scan imagining.

From optical theory, for unit magnification over Area A with uniform illumination $I_o$, where the reflectivity function per unit volume of media is $\Delta(X,Y,Z)$, and the imaging system f-number is F, the total reflected light intensity at the image plane I (X,Y,) is given by equation (1):

$$I(X, Y) \propto \int_Z \int_{A(Z)} \frac{I_o \rho(X, Y, Z) dA dZ}{\left[\left(\frac{Z}{2F}\right)^2 + (\lambda F)^2\right]} \quad (1)$$

The function of Z, obtained by first integrating over the area at each Z plane, is a "range gate" which describes sensitivity to scatter from regions above or below the focal plane. Actual evaluation of these integrals is made rather complex by aperture shape. However, the approximate dependence of the area integrals on Z can be found by inspection. The intensity of the defocused reflected light at each pixel drops off as $Z^{-2}$. The area producing this illumination on that pixel increases with $Z^2$. This occurs at every layer in the sample. Integrating just over area, the resulting range gate function is approximately constant, i.e., independent of Z. This means there is no effective range gate. Every layer in the resulting image is weighted only by it intrinsic reflectivity. Unless the reflectance is strongly confined to a region very near the focal plane, the image contrast is quickly overwhelmed by defocused light.

The MTF can written as a function of spatial frequency (k) as given in equation (2):

$$MTF = \frac{[I_{max}(k) - I_{min}(k)]}{[I_{max}(k) + I_{min}(k) + 2I_{defocus}]} \quad (2)$$

where $I_{min}(k)$ and $I_{max}(k)$ give the ideal focal plane contrast at given spatial frequency, and the defocused light intensity shows the effect of background light on contrast: $I_{defocus}$ increases directly with Z-thickness in a uniformly scattering medium. Therefore, the full field imaging method is unsuitable in scattering media where the thickness of the sample is greater than the depth of field scale ($8F^2$). Contrast is halved when volume-integrated scattering anywhere in the optical path is equal to the focal plane reflection. This is the source of the sensitivity of conventional fundus image contrast to media clarity.

FIG. 4B shows the optical effect of defocusing in a confocal "flying spot" system of the prior art. The equation for the intensity I (X,Y) remains the same except for a modification as a consequence of focusing the illuminating laser light to a point confocal with the aperture. This adds an identical defocus factor in the denominator in equation (1). The range defocus light falls off as $Z^{-4}$, rather than $Z^{-2}$. Integrating over area, the resultant range gate function has dimensions of $Z^{-2}$. The full gate width at half maximum is just the usual definition of the depth of field. This weighting of $\Delta$ is integrable in Z, so that uniform scattering from surrounding tissue will not destroy focal plane image contrast. The confocal flying spot method of the prior art provides intrinsic sectioning properties, limited only by extinction due to absorption and scatter.

FIG. 4C illustrates the optical effect of defocusing in a line scanning imaging system such as the LSLO of the invention. For a line scanning system, the system focuses the laser light 435 to a line confocal with the linear detector array 440 by use of optical components 450 In this configuration, the illumination intensity falls off as $Z^{-1}$. The defocused intensity therefore falls off as $Z^{-3}$. Integrating over area, the resultant range gate function has $Z^{-1}$ dependence, with a gate width proportional to the depth of field. However, this weighting of $\Delta$ is not integrable in Z. Rather, it has only a weak logarithmic divergence. Uniform scattering from surrounding tissue will reduce focal plane image contrast. Nevertheless, a line scanning system provides useful sectioning properties, because contrast falls off much less rapidly in thick samples, and is far less sensitive to more remote media opacities.

Laser imaging systems generally tend to exhibit speckle patterns, and this is so for both the SLO and the LSLO. Except near smooth interfaces with changes in refractive index, biological systems tend to scatter light from spatially distributed sites, with sizes and separations from nanometers to microns. Because the laser light is spatially coherent, this means that the phase relationships of the reflections along the beam (at least within one coherence length) are preserved. The total intensity of the light collected from such a region is the coherent sum of many contributions. The random walk nature of the amplitude sum leads to constructive and destructive interference with large variations in power falling on the aperture or on each pixel, especially if the aperture or the pixel size is near the diffraction limit. The diffraction limit can be thought of as "one speckle" in the transverse direction. This effect is frequently countered by using a less confocal (larger) aperture collecting light over a larger area which tends to average away some speckle. This solution is not available for the LSLO, and LSLO imaging is roughly equivalent to so-called "tightly confocal" SLO imaging. The effective image resolution is roughly halved in the coherent case.

A significant improvement is realized by using superluminescent diode illumination. Current commercial devices with 25 nm bandwidth and ~10 μm coherence length are available at low prices, with power levels of a few milliwatts. Over the depth of field in the tissue, the speckle will substantially average away, producing smoother less granular images without loss of transverse resolution.

The light gathering behavior of a LSLO embodying principles of the invention is compared to a standard point-scanning system. The model used for calculation assumes identical optical geometries and detector quantum efficiencies. Both systems are modeled to scan vertically at the framing rate. For a 500×500 image at 30 Hz framing rate, the horizontal scan rate $f_H$, of the SLO is 15 kHz. The "flying spot" detector requires a bandwidth of $f_H$ times the number of pixels per line, $N_{Hpix}$. To resolve 500 horizontal pixels at 15 kHz, the bandwidth is more than 10 MHz. This can be achieved because the full power of up to a few milliwatts is focused at the retina confocally with the detector aperture. The reflected power collected depends upon the incident power $P_I$ (say 1 mW), the local reflectance, $R(X,Y)$, of the retina (less than 10% in NIR), and the collection solid angle $\Omega$ (~$10^{-3}$ sr). This amounts to a typical range from about 1 to about 100 nW. The noise-equivalent power (NEP) of the silicon detector is one noise contribution, and another is shot noise. An acceptable signal-to-noise ratio SNR is easily reached within the required bandwidth. The dynamic range of 8-bit images requires a SNR >255 to fully utilize the available range, that is, a noise level less than the signal strength represented by the least significant bit.

$$SNR = \frac{[\eta R(X,Y)\Omega P_I]^2}{NEP(f_H N_{Hpix}) + (\eta R\Omega P_I E_v f_H N_{Hpix})} \quad (3)$$

where η is the quantum efficiency and $E_v$ is the energy per photon at the illuminating wavelength. The thermal noise of a small silicon photodetector can be ~$10^{-15}$ W/(Hz)$^{1/2}$. Readout noise of a read-out amplifier will usually dominate the NEP for silicon photodetectors. Depending upon collected power, the SNR may be limited by either detector/amplifier noise or shot noise. When dominated by shot noise the SNR becomes $$SNR = \left[\frac{\eta R\Omega P_I}{E_v f_H N_{Hpix}}\right] \quad (4)$$

The LSLO images an entire line at once. No transverse scan is required. The readout of the linear CCD array represents a "scan," but it can be performed during the time that the line is repositioned. The effective integration time is $1/f_H$, instead of $1/f_H N_{Hpix}$ as for the flying spot system. For the same average power at the retina, the line scanner must spread the beam with a cylindrical optic to form a line covering all $N_{Hpix}$ at once. In other words, the power at each pixel is reduced in proportion to the number of pixels: $P_I$ per pixel for the SLO becomes $P_I/N_{Hpix}$ for the LSLO. Therefore the equation, and the shot-noise limited SNR, is unchanged and the line scan and flying spot systems are equivalent as regards SNR. However, because the instantaneous power per pixel is smaller by $N_{Hpix}$ for the LSLO, while the detector/amplifier NEP term only drops by $(N_{Hpix})^{1/2}$, the detector/amplifier thermal noise contribution is $(N_{Hpix})^{1/2}$ times greater. High quality linear CCD arrays/amplifiers are able to operate near the shot noise level of a few hundred photoelectrons before other noise sources become important. Excessive noise would appear as snow over the acquired images, over and above the speckle noise. No such noise has been observed at the quoted eye-safe light levels.

The model can also be extended to evaluate the full image case of the prior art. For a square CCD array in full field operation, the power level per pixel is reduced still further by another factor of $N_{lines}(\approx N_{Hpix})$. The detector/amplifier noise is most likely to dominate, and CCD imaging becomes noisy at these low eye-safe light levels. Flash fundus imaging or higher illumination powers must be used, and all confocal advantages are lost.

The operation of the LSLO has been tested to determine the resolving power and diffraction limits of the system, using both biological samples, such as an eye, and inanimate, mechanically produced targets.

The width, w, of the laser line beam at the retina, (to the first null in the Line Spread Function) is given by:

w/2 π8$f_{eye}$/d~38 microns with the Volk 66, or ~19 microns with the 30D, for the eye, and w/2 8$f_{model}$/d~42 microns with the Volk 66, or ~21 microns with the 30D, for the model eye.

In one embodiment, the best focused beam width based on resolution targets appears to be somewhat larger. This is attributable in part to aberrations in some non-optimized elements with the optical train, and perhaps to forward scatter from optical surfaces. The pixel size referenced to the retina is designed to roughly match these beam widths. For the Volk 66 and 30D, the pixel diagonals at the model retina are 40 μm and 20 μm respectively. The horizontal and vertical Nyquist limit is twice the pixel spacing or 56 μm and 28 μm for the two magnifications, or 17 and 35 line pairs per millimeter.

With a fixed 3 mm eye entrance pupil, or ~7 mm and 14 mm at the pupil conjugate for the Volk 66 and 30D respectively, the Airy diffraction at the CCD array due to the 40 mm objective is 11.7 μm and 5.8 μm. To first approximation, the net double-pass image optical resolution element is the root-mean-square sum of these contributions, or 58 μm and 29 μm. This closely matches the Nyquist limit of the pixel array.

Figure 5A:
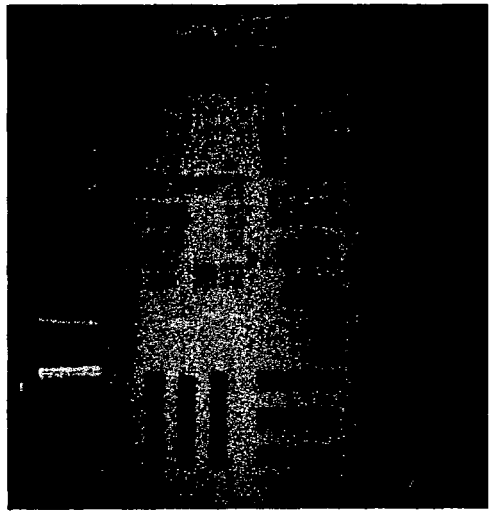
FIGS. 5A and 5B show the standard prior art United States Air Force (U.S.A.F.) resolution target #51 at low and high magnification, respectively.
Figure 5B:
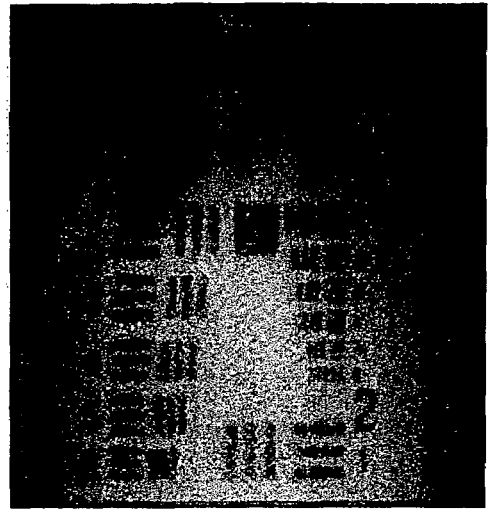

FIGS. 5A and 5B show the standard United States Air Force (U.S.A.F.) resolution target #51 at low and high magnification, respectively. Because the model eye consists of an achromat in front of the planar target, ophthalmoscopic lenses overcorrect for field curvature that would be present in the eye. The bright central region is due to field curvature moving target plane out of the depth of field at high scan angles. Resolution is determined by reading off the group and line number of the smallest resolvable line triplet.

Despite some focus irregularities of the Volk 66 lens interacting with the model eye optics, the resolutions, judging from the limits of visibility of the U.S.A.F. target triplets, are:

For low magnification 40 degree field: group 2, line 6, corresponding to 7 line pairs per mm or 143 µm per line pair For high magnification 20 degree field: group 3, line 6, corresponding to 14.3 line pairs per mm or 70 µm per line pair.

Figure 6A:
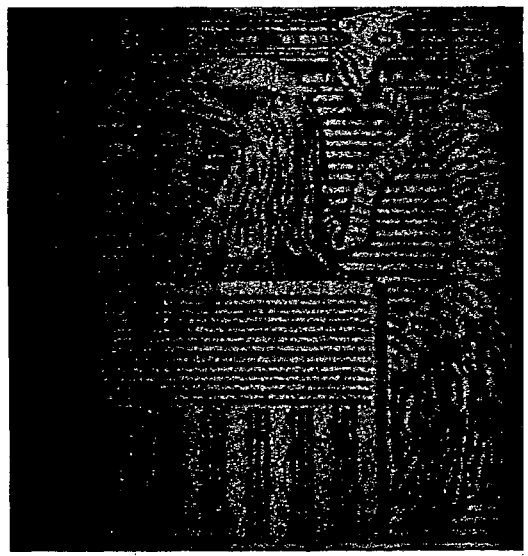
FIGS. 6A and 6B show prior art target images that appear on the reverse of a United States one dollar bill.
Figure 6B:
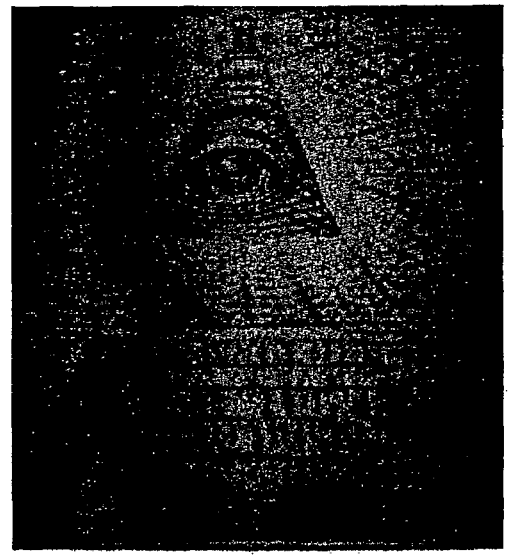

In each case approximately 5 pixels can be counted between lines at the limiting resolution. These resolution values are approximately twice the calculated incoherent values, as expected. The contrast is expected to vanish near the Nyquist limit, and the threshold of visibility for coherent illumination will always lie somewhat above this limit, usually a factor of two. The slight translucence of the matte target surface itself gave rise to apparent reduction of the contrast having nothing to do with LSLO optics, as well as a highly speckled appearance, which has an adverse impact on apparent resolution. Denser targets (e.g. images that appear on the reverse of a United States one dollar bill) placed directly at the first retinal conjugate (no Volk lens) have an improved appearance as in FIGS. 6A and 6B. Another interesting effect observed is the difference in contrast between the horizontal and vertical bars, seen clearly in FIG. 5B. This can be understood as the effect of the proximity of bright pixels to the left and right on the imaged line. The vertical bars, being only two or three pixels wide have considerable background contributions from the neighboring bright regions, whose PSF extends over two pixels. However, on the horizontal dark lines, adjacent pixels on the line are dark except at the ends of the lines, with little or no consequences for contrast.

The widths of the laser line were w/2 n8f/d~40 microns with the Volk 66, or ~20 microns with the 30D. The length of the laser line was set to cover the fields of interest of about 40 degree and 20 degree horizontal. In order to have minimal variations in brightness along the 7 mm CCD array, the FWHM has been scaled via the focal length of the fixed cylindrical lens, to no less than 7 mm at the model retina. Approximately 1 mW of power falls fairly uniformly on the central 7 mm of the line, which is useful for power density calculations in the worst case (e.g., use of the 30D optic):

Length, L~0.7 cm.

Stationary Line Power Density at the retina 1 mW/(wL) ~500 mW/cm$^2$. Safe exposure times at such power densities at 830 nm is at least 10 seconds, and consistent with the time needed to for the subjects to avert their gaze, or for the operator to block the incoming light or turn off the light source in the event of scanner failure.

A plane wave equivalent at the cornea can be estimated by determining the power at the cornea which corresponds to this power density on a single 30×30 micron spot, i.e., one virtual laser element of the line. This is simply $\frac{1}{250}^{th}$ of the incident power, or less than about 4 µW.

When scanned vertically through 0.7 cm to form a square image, the time average power density at the retina drops further to less than $\frac{1}{300}^{th}$ of this power: Average Power Density of laser line scan (full field 7 mm×7 mm)~2 mW/cm$^2$.

The key safety feature of the LSLO is that even if the vertical scanner fails, no laser interlock is needed because the stationary line itself is eye-safe over the few seconds required to move the volunteer's eye away. The fixed cylindrical optic, which cannot be removed without disassembling the instrument, ensures that the power density at the retina can never be greater that the quoted values.

The LSLO of the invention has been compared with SLOs of the prior art through the acquisition of wide field images. Forty degree field LSLO images in the left and right eyes of a human subject are shown in FIG. 7. Sharp images were obtained with the LSLO, and typical characteristics of confocal infrared image were seen: a dark disc, well-resolved bright vessel lumen, lighter arteries and darker veins, foveal reflex in some subjects, capillaries and choroidal vessels, and variations in pigmentation. The left eye above shows a retinal scar and some residual features of prior central serous retinopathy. Because of the relatively small pupil required for these images and the modest depth of field, clear images can be obtained well into the periphery. For comparison, a standard SLO image of the prior art at slightly higher magnification is shown in FIG. 8.

Figure 9A:
FIG. 9 shows twenty degree field LSLO images in a human subject, according to principles of the invention.
Figure 9B:
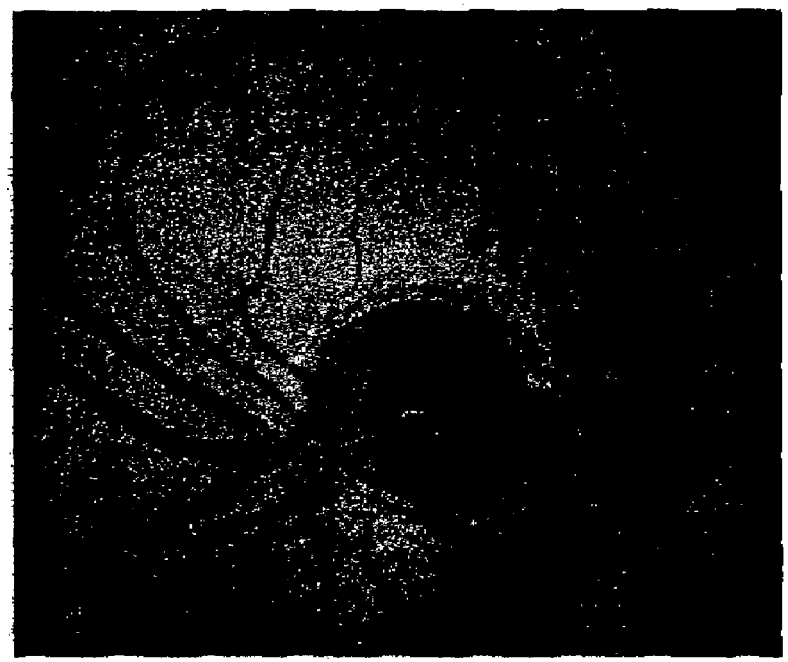

The capabilities of the LSLO of the invention are demonstrated by recording macular and disc images. A selection of twenty degree field LSLO images in a human subject are shown in FIG. 9. The images distinctly show veins and arteries, retinal nerve fiber foveal reflex, and other morphology.

In some embodiments, the LSLO provides the ability to collect stereo pairs. In conventional stereo imaging, the pupil aperture is optically split and two images are captured corresponding to the left and right fields. The parallax between the images contains the depth information. Depth of field is determined by the numerical apertures of the individual fields. Because of the finite depth of field of the LSLO with different viewing angles, it is equally effective at gathering depth information. But in addition, due to its confocality, defocused light from above and below the plane of focus is suppressed. This allows superior 3D visualization of deeper retinal structures.

FIG. 10 shows illustrative disc image pairs captured in succession with the LSLO, with an approximately 1 to 2 mm lateral shift in pupil position. This purely lateral pupil shift allowed the same image to be captured at two viewing angles separated by 3 to 6 degrees and is an effective simulation of anticipated live-motion, split-pupil aperture binocular LSLO operation. These images are displayed side-by-side in FIG. 10 at the appropriate separation, so that when viewed from 2 feet (60 cm) or more from the page, the image can be made to fuse in a stereo view.

In FIG. 10, the shapes and orientations of the vessels near the disc are clearly visible. Left/right focus is slightly different due to successive image capture. The perception of a mild fogginess in the images is due to the low resolution in the images (500×512), and speckle. High resolution images, and perhaps super luminescent diode (SLD) illumination, should greatly reduce granularity.

FIG. 11 shows a demonstration of confocal and anterior segment imaging. The image of FIG. 11 was obtained when the ophthalmoscopic objective was removed and the anterior segment of the subject's eye was placed at the conjugate image plane.

An embodiment of the LSLO of the invention preferably operates at two magnifications, and is configurable to permit imaging of an anterior segment and non-mydriatic imaging of the posterior segment. In one embodiment, this is accomplished using one of two interchangable ophthalmoscopic lenses with rotary focus. In other embodiments, the ophthalmoscopic lenses are demountable, and can be interchanged, or the LSLO can be operated without an ophthalmoscopic lens. The LSLO device incorporates all necessary electronics and optics for image acquisition, without the need for external image acquisition, a computer or a CRT. The LSLO device provides on-board camera captured image storage and image downloading.

In some embodiments, the use of two substantially similar instruments together can provide additional functionality. Dual channels can be integrated that can be configured for multi-wavelength operation and real time binocular imaging. Wearable micro-display technology permits the operator to manipulate the device with an unobstructed visual field, while glancing a few degrees off axis, such as upward or downward, to the color/stereo (left and right eye) display. The displays appear to merge near the hand-held device so that minimal accommodation is needed while shifting gaze from patient to stereo display. The use of an adjustable facial support system or mask, which makes possible the operator gently holding the apparatus in place adjacent to the patient, provides all the stability and articulation that the lightweight LSLO needs for patients in any orientation.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An optical apparatus comprising:
   at least one lens through which a line of light is directed to a portion of an eye;
   an optical element that (i) scans, through at least one of the lenses, a portion of the eye with the line of light in a direction perpendicular to the line, and (ii) descans light returning from the portion of the eye illuminated in a line focus configuration to a linear array detector; and
   at least one optical component that confocally images the light to the linear array detector.

2. The optical apparatus of claim 1 wherein the at least one optical component comprises a beam separator that receives the light returning from the portion of the eye illuminated and that redirects the light to the linear array detector to confocally image the light.

3. The optical apparatus of claim 1 wherein the optical element comprises a mirror.

4. The optical apparatus of claim 1 wherein the at least one optical component comprises line imaging optics to provide output light in the line focus configuration.

5. The optical apparatus of claim 1 wherein the at least one optical component comprises a pupil stop that prevents unwanted light from propagating through the optical, apparatus.

6. The optical apparatus of claim 5 wherein the pupil stop is adapted to prevent non-confocally received light from propagating through the optical apparatus.

7. The optical apparatus of claim 1 wherein the at least one optical component comprises a beam separator positioned conjugate a cornea of the eye; and the optical element includes a scanning mirror positioned conjugate a pupil of the eye.

8. The optical apparatus of claim 1 further comprising:
   a light source providing a substantially point source of light; and
   a second at least one lens receiving the light from the point source and providing the line of light.

9. The optical apparatus of claim 1 further comprising:
   a second optical element to split descanned light returning from the illuminated portion of the eye into a first beam of light and a second beam of light, the linear array detector receiving the first beam of light; and
   a second detector to receive the second beam of light.

10. The optical apparatus of claim 9 wherein the first beam of light and the second beam of light are collected to form a stereo image of the eye.

11. A method of making an optical measurement of an eye, comprising:
    scanning, through at least one lens, a portion of the eye with a line of light in a direction perpendicular to the line of light using an optical element;
    confocally imaging light returning from the illuminated portion of the eye; and
    descanning the light returning from the illuminated portion of the eye to a linear array detector in a line focus configuration using the optical element.

12. The method of claim 11 further comprising separating light incident on the eye and light reflected from the eye.

13. The method of claim 11 further comprising synchronously scanning the line of light and receiving reflected light with a mirror using the optical element.

14. The method of claim 11 further comprising using an aperture to prevent unwanted light from propagating through the optical apparatus.

15. The method of claim 14 wherein the unwanted light comprises non-confocally received light.

16. The method of claim 11 further comprising:
    dividing descanned light returning from the illuminated portion of the eye into a first beam of light and a second beam of light;
    receiving the first beam of light at the linear array detector; and
    receiving the second beam of light at a second detector.

17. The method of claim 16 further comprising forming a stereo image of the eye from the first beam of light and the second beam of light.

18. An optical apparatus comprising:
    at least one lens through which a line of light is directed to a portion of an eye;
    a mirror to scan, through at least one of the lenses, the portion of the eye with the line of light in a direction perpendicular to the line and to descan light reflected from the portion of the eye illuminated to a detector; and
    a beam separator to receive the light from the mirror and direct the light to the detector.

19. The optical apparatus of claim 18 further comprising line imaging optics to provide the light to the detector in a line focus configuration.

20. The optical apparatus of claim 18 wherein the beam separator and the mirror are adapted to form separate paths for light incident on the eye and for light returning from the eye.

21. The optical apparatus of claim 20 wherein the beam separator prevents unwanted light from propagating through the optical apparatus to the detector.

22. The optical apparatus of claim 18 further comprising:
    an optical element to split light redirected by the beam separator into a first beam of light and a second beam of light, the detector receiving the first beam of light; and
    a second detector to receive the second beam of light.

23. The optical apparatus of claim 22 wherein the first beam of light and the second first beam of light are collected to form a stereo image of the eye.

24. A line scanning laser ophthalmoscope comprising:
  means for scanning, through at least one lens, a portion of the eye with a line of light in a direction perpendicular to the line of light, and descanning light returning from the illuminated portion of the eye to a linear array detector in a line focus configuration;
  means for confocally imaging the light returning from the illuminated portion of the eye to the linear array detector; and
  means for splitting the light returning from the illuminated portion of the eye into a first beam of light and a second beam of light, the linear array detector receiving the first beam of light and a second detector receiving the second beam of light.

25. The optical apparatus of claim 24 wherein the first beam of light and the second beam of light are collected to form a stereo image of the eye.

26. An optical apparatus comprising:
  at least one lens through which a line of light is directed to a portion of an eye;
  at least one optical component that (i) scans, through at least one of the lenses, a portion of the eye with the line of light in a direction perpendicular to the line, (ii) confocally images light returning from the portion of the eye illuminated, and (iii) descans light returning from the portion of the eye illuminated in a line focus configuration;
  an optical element to split descanned light returning from the portion of the eye illuminated into a first beam of light and a second beam of light;
  a first detector to receive the first beam of light; and
  a second detector to receive the second beam of light.

27. The optical apparatus of claim 26 wherein the first beam of light and the second beam of light are collected to form a stereo image of the eye.

\* \* \* \* \*